(12) United States Patent
Dutoit et al.

(10) Patent No.: US 7,837,709 B2
(45) Date of Patent: Nov. 23, 2010

(54) BONE FIXATION MEANS

(75) Inventors: Christof Dutoit, Solothurn (CH);
Christoph Fürst, Lohn-Ammannsegg (CH)

(73) Assignee: Synthes USA, LLC, West Checter, PA (US)

( * ) Notice: Subject to any disclaimer, the term of this patent is extended or adjusted under 35 U.S.C. 154(b) by 819 days.

(21) Appl. No.: 10/591,548

(22) PCT Filed: Mar. 3, 2004

(86) PCT No.: PCT/CH2004/000119

§ 371 (c)(1),
(2), (4) Date: Jun. 26, 2007

(87) PCT Pub. No.: WO2005/084568

PCT Pub. Date: Sep. 15, 2005

(65) Prior Publication Data

US 2008/0021453 A1 Jan. 24, 2008

(51) Int. Cl.
*A61B 17/04* (2006.01)

(52) U.S. Cl. .................................... 606/232; 606/66

(58) Field of Classification Search .............. 606/65, 606/66, 60, 280, 281, 286, 232; 623/22.11–22.19; 411/166, 81; *A61B 17/56, 17/58; A61F 2/30, A61F 2/32*
See application file for complete search history.

(56) References Cited

U.S. PATENT DOCUMENTS

| | | | | |
|---|---|---|---|---|
| 3,374,786 A | * | 3/1968 | Callender, Jr. | 606/65 |
| 3,996,931 A | * | 12/1976 | Callender, Jr. | 606/65 |
| 4,432,358 A | | 2/1984 | Fixel | |
| 4,530,355 A | | 7/1985 | Griggs | |
| 4,940,467 A | * | 7/1990 | Tronzo | 606/66 |
| 5,522,817 A | * | 6/1996 | Sander et al. | 606/329 |
| 5,725,597 A | * | 3/1998 | Hwang | 623/22.15 |
| 5,741,256 A | | 4/1998 | Bresina | |
| 5,769,852 A | * | 6/1998 | Br.ang.nemark | 606/65 |
| 5,772,662 A | * | 6/1998 | Chapman et al. | 606/281 |
| 5,827,285 A | * | 10/1998 | Bramlet | 606/60 |
| 5,908,422 A | | 6/1999 | Bresina | |
| 5,976,139 A | | 11/1999 | Bramlet | |
| 6,022,352 A | * | 2/2000 | Vandewalle | 606/286 |
| 6,187,007 B1 | | 2/2001 | Frigg et al. | |
| 6,221,107 B1 | * | 4/2001 | Steiner et al. | 623/13.14 |

(Continued)

FOREIGN PATENT DOCUMENTS

CA    2 405 235    2/2001

(Continued)

OTHER PUBLICATIONS

International Search Report of PCT/CH2004/000119.

*Primary Examiner*—Pedro Philogene
(74) *Attorney, Agent, or Firm*—Fay Kaplun & Marcin, LLP (57) ABSTRACT

The invention relates to a bone fixation means (1) comprising: A) a longtitudinal shaft (2) with longtitudinal axis (3), and; B) an anchoring element (4), which can be fixed inside a bone and which has the same longitudinal axis (3) and is characterized in that; C) interacting means (5; 6) are provided on the shaft (2) and on the anchoring element (4), which either permit or prevent a rotation of the anchoring element (4) about the longitudinal axis (3) relative to the shaft (2).

25 Claims, 9 Drawing Sheets

U.S. PATENT DOCUMENTS

| | | |
|---|---|---|
| 6,406,477 B1 | 6/2002 | Fujiwara |
| 6,533,789 B1 | 3/2003 | Hall, IV et al. |
| 6,645,209 B2 | 11/2003 | Hall, IV et al. |
| 6,835,197 B2 | 12/2004 | Roth et al. |
| 7,556,629 B2 * | 7/2009 | von Hoffmann et al. ...... 606/67 |
| 2004/0215200 A1 * | 10/2004 | Tornier et al. ................. 606/91 |

FOREIGN PATENT DOCUMENTS

| | | |
|---|---|---|
| EP | 0 655 224 A | 5/1995 |
| JP | 2003-506189 | 2/2003 |
| WO | WO 98/05263 A1 | 2/1998 |
| WO | WO 02/00123 A1 | 1/2002 |

* cited by examiner

BONE FIXATION MEANS

BACKGROUND OF THE INVENTION

The invention relates to a bone fixation means of the introductory portion of claim 1.

Such bone fixation means are used, for example, for the medical care of fractures at the proximal femur, particularly of trochanteric fractures and fractures of the neck of the femur. Such devices comprise essentially a bone plate, which can be fixed to the femur with an angular sleeve, which is to be brought into the neck of the femur for accommodating the shaft of the bone fixation means in a rotationally stable manner.

All the known hip screws, which are to be used with bone plates that can be fastened to the femur, have the disadvantage that their out-of-round shaft, which is to be introduced into the sleeve of the bone plate, is firmly connected with the anchoring element (screw or blade) of the bone fixation means.

If, after the implantation of the hip screw, the surgeon wishes to guide the out-of-round sleeve of the bone plate over the out-of-round shaft of the hip screw, then the bone plate of the DHS is not parallel to the femur and, instead, must be rotated into this position, the hip screw, captured in the sleeve, being rotated along. Accordingly, the hip screw is screwed further forward or back a little once again. This advance or retraction is impermissibly large especially in the case of implants employing blades which have a steep pitch, the so-called helical blades.

For hip screws, with a conventional, flat thread, the shaft of the screw can be aligned without problems so that the sleeve tab, when pushed over the out-of-round shaft of the screw, automatically lies parallel to the femur. Normally, once it has been turned upside down over the sleeve, the plate is not rotated further.

In the case of helical blades with a steep pitch (helix), this alignment is difficult, since such implants translate a large distance in or out when rotated only a small amount.

SUMMARY OF THE INVENTION

The invention is to provide a remedy here. It is an object of the invention to provide a bone fixation means, which comprises a lockable coupling, which can be unlocked, between the shaft and the anchoring element of the bone fixation means, so that the shaft can be rotated relative to the anchoring element about the longitudinal axis or locked rotationally.

Pursuant to the invention, this objective is accomplished with a bone fixation means, which has the distinguishing features of claim 1.

The advantages, attained by the invention, are, essentially, the following:

The present invention permits bone fixation means with novel anchoring elements to be used, such as, for example, helical blades with a steep pitch (helix), in combination with a conventional sleeve tab, such as those, which have been on the market for more than 20 years already.

The compatibility between the new bone fixation means and the conventional tabs permits the surgeon to make a decision in the course of the surgery between conventional bone screws and the new bone fixation means.

In a preferred embodiment, the bone fixation means comprise axial locking-in-position means, by means of which the shaft and the anchoring element are held together axially. With that, the advantage can be achieved that, during the implantation of the bone fixation means, the anchoring element may be rotated relative to the shaft, while, nevertheless, the two parts are held together axially and cannot fall apart.

The axial locking-in-position means and the interacting means may be realized partly or completely from the same elements or may also be configured independently of one another. Moreover, the axial locking-in-position means may or may not be detachable. It may be possible to snap the axial locking-in-position means in-place or the latter may comprise radially elastic blades with elevations, which can be snapped into grooves, so that a simple assembly of shaft and anchoring element can be attained.

In a different embodiment, the blades are disposed at the anchoring element and the groove at the shaft. The elevations preferably are convex and can be snapped into a ring-shaped groove.

In yet another embodiment, the axial locking-in-position means comprise two pins, which penetrate the cavity wall diametrically at the end of the anchoring element and the tips of which engage a groove at the shaft, the groove being concentric with the longitudinal axis. With that, a construction of the axial locking-in-position means, which is simple to produce, can be attained.

In a further embodiment, aligned annular grooves for accommodating a retaining ring, concentric with the longitudinal axis, are provided at the cavity wall at the rear end of the anchoring element and at the shaft.

The interacting means may be equipped frictionally or positively. In the case of a frictional configuration, the following, for example, are suitable:

conical elements, which may be wedged in a complementary conical borehole. In one embodiment, the conical elements are hammered in. In a different embodiment, the conical elements are wedged with the help of a screw mechanism. In yet another embodiment, the conical element is provided with a conical external thread and the conical borehole with an internal thread. Conical elements, which can be hammered in, make a simple configuration of the coupling possible, whereas the last-described conical connection represents a simple detachable variation; or radially elastic blades, which are mounted, for example, at the anchoring element and can be placed by means of a conical screw against the wall of the central borehole in the shaft. The simple way of handling the interacting means is advantageous here.

In the case of a positive configuration of the interacting means, denticulations, for example, which may be mounted at the shaft and at the anchoring element, preferably at the end face, and be brought into mutual engagement, are suitable.

In one embodiment, one of the denticulations is mounted firmly at the anchoring element while the second denticulation is mounted at a fixation element, which is axially displaceable and locked in position rotatably at the shaft. The fixation element can be shifted axially by means of a screw, which can be rotated from the free end of the shaft.

In a different embodiment, one of the denticulation's is disposed at ring element at the shaft, which is locked in position rotationally, whereas the second denticulation is mounted at a fixation element, which is also locked in position rotationally, but can be shifted axially. The fixation element can be shifted axially analogously by means of a screw, which can be rotated from the free end of the shaft, until the denticulations are in mutual engagement or are remote from one another.

The anchoring element may be constructed as a screw with a thread lead of more than 50 mm and preferably of more than 80 mm.

The use of a helical blade has numerous clinical advantages over the use of a conventional hip screw:
a) Cutting of the implant out of the bone is avoided by the larger contacting surface.
b) As the helical blade is hammered into the head of the femur, the bone material is compressed around the implant. This additionally minimizes the risk that the implant will cut out from the bone.
c) In contrast to the conventional screw, the helical blade prevents rotation of the head of the femur on the implant.

In a further embodiment, the shaft of the bone fixation means is constructed out-of-round when viewed in a cross-section, which is orthogonal to the longitudinal axis. With that, the advantage can be attained that sleeve tab can be inverted over the out-of-round shaft of the bone fixation means, independently of the extent to which the bone fixation means was bought in to the head of the femur. The bone fixation means thus can be brought in two the optimum position in the head of the femur and then anchored rotationally stably.

In one embodiment, the fixation device for the osteosynthesis comprises a bone plate, which can be fastened to the femur, with an angularly adjoining sleeve, which is suitable for accommodating the shaft of the bone fixation means. Preferably, the shaft is provided on the outside and the sleeve on the inside with complementary, out-of-round cross sections.

Further advantageous developments of the invention are characterized in the dependent claims.

BRIEF DESCRIPTION OF THE DRAWINGS

The invention and further developments of the invention are described in even greater detail in the following by means of partially diagrammatic representations of several examples. In the drawing.

DETAILED DESCRIPTION OF THE INVENTION

In FIGS. 1 to 4, different embodiments of the inventive bone fixation means 1 are shown with a coupling 37 between the shaft 2 and the anchoring element 4, the coupling 37 comprising axial locking-in-position means 12 (FIGS. 2a to 2k) and means 5; 6 (FIG. 3, 4), which make a rotationally locking-in-position possible. In this connection, the interacting means 5; 6 can make possible a frictional locking (FIGS. 3a to 3g) or a positive locking (FIGS. 4a to 4d) of the relative rotational movement between the shaft 2 and the anchoring element 4.

In the embodiments shown in FIGS. 1a to 1d, the anchoring element 4 is shown as a spiral blade, which is coaxial with the longitudinal axis 3 and equipped with four helical blades 7, which are distributed over the periphery, the depression 8 between the blades 7 at the free end 9 of the anchoring element 4 being open. The radial depth of the depressions 8 remains constant on an axial length L and then decreases continuously, until the depressions 8 at the fixed end 10 of the anchoring element 4 changes over into the circumferential surface 11 of the latter. On its circumferential surface 38, the shaft 2 is provided with two flat spots 39, which are disposed diametrically opposite to one another and are parallel to the longitudinal axis 3, so that the shaft 2 can be secured in a complementary borehole of a sleeve 49 (FIG. 5) to prevent rotation about the longitudinal axis 3.

FIGS. 2a to 2k show embodiments of the axial locking-in-position means 12 in detail. They are part of the coupling 37 (FIG. 1). The axial locking-in-position means 12 only bring about an axial fixation between the shaft 2 and the anchoring element 4, the rotation of the anchoring element 4 relative to the shaft not being impeded.

Figure 2A:
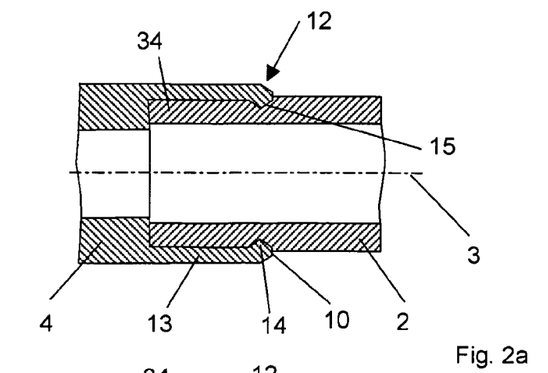
FIG. 2a shows a diagrammatic representation of the axial locking-in-position means of the embodiment of the inventive bone fixation means shown in FIG. 1a, FIG. 2b shows a diagrammatic representation of the axial locking-in-position means of the embodiment of the inventive bone fixation means shown in FIG. 1b.

For the embodiment of the axial locking-in-position means 12, shown in FIG. 2a, the latter comprise four blades 13, which are disposed at the fixed and 10 of the anchoring element 4, distributed uniformly over the periphery and aligned parallel to the longitudinal axis 3 and which can be pushed axially over the fixed end 34 of the shaft 2 and connected with the shaft 2. These blades 13 can be deformed elastically transversely to the longitudinal axis 3 and, internally, have radial elevations 14, which can be snapped into a groove 15, which extends over the whole of the periphery of the shaft 2 and is V-shaped in cross section. The axial locking-in-position means 12 bring about an axial fixation of the shaft 2 relative to the anchoring element 4 in both directions without impeding the free rotation of the anchoring element 4 relative to the shaft 2 about the longitudinal axis 3.

Figure 2B:
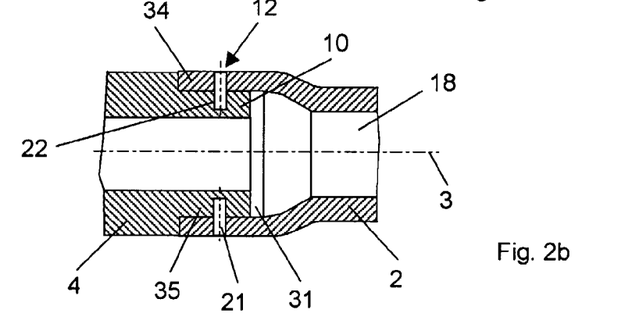

The embodiment of the axial locking-in-position means 12, shown in FIG. 2b, comprises two locking-in-position pins 21, which, at the fixed end 10 of the shaft 2, are mounted radially in the wall of the shaft 2, and the tips of which protrude radially into the first, expanded segment 31 of the central borehole 18 in the shaft 2 and are captured axially there in a groove 22 extending peripherally on the outside of the peg 35. Since this groove 22 extends over the whole of the periphery of the peg 35, the rotation of the shaft 2 relative to the anchoring element 4 is not impeded by the two locking-in-position pins 21.

Figure 2C:
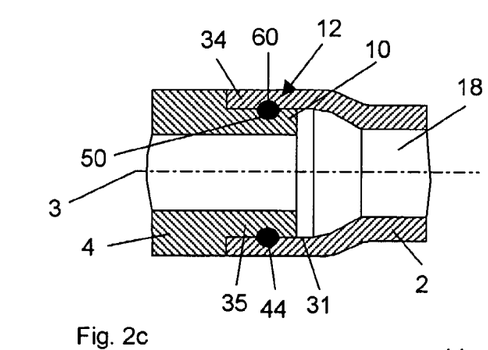
FIG. 2c shows a diagrammatic representation of the axial locking-in-position means of the embodiment of the inventive bone fixation means shown in FIG. 1c.
Figure 2D:
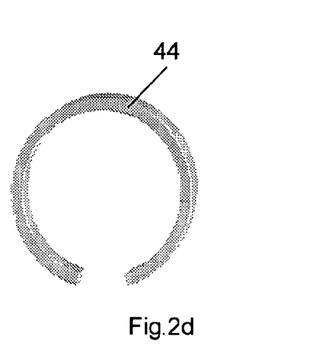
FIG. 2d shows a perspective representation of the embodiment of a retaining ring of the locking-in-position means shown in FIG. 2c.
Figures 2E, 2F:
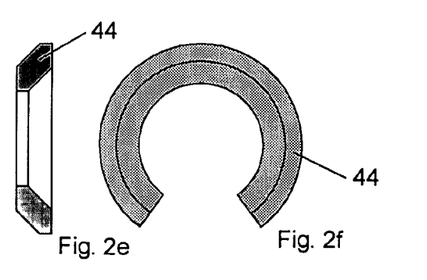
FIG. 2e shows a section through a different embodiment of a retaining ring for the embodiment of the inventive bone fixation means shown in FIG. 2c.
FIG. 2f shows a view of the embodiment of a retaining ring, shown in FIG. 2e.
Figure 2G:
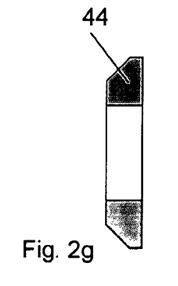
FIG. 2g shows a section through a further embodiment of a retaining ring for the embodiment of the inventive bone fixation means shown in FIG. 2c.
Figure 2H:
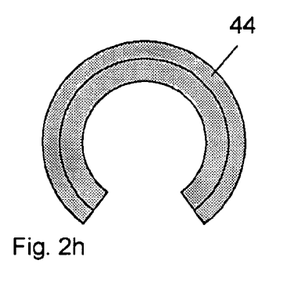
FIG. 2h shows a view of the embodiment of a retaining ring shown in FIG. 2g.

For the embodiment, shown in FIG. 2c, the axial locking-in-position means 12 are realized by a retaining ring 44, which is inserted into two concentric annular grooves 50; 60. The annular grooves 50; 60 are disposed in such a manner that, at the outside, at the peg 35, analogously to the embodiment shown in FIG. 2b, a peripherally extending first annular groove 50 and, in the expanded segment 31 of the central borehole 18 in the shaft 2, a second, peripherally extending annular groove 60 are disposed. The retaining ring 34, placed in these two annular grooves 50; 60, prevents relative axial movement between the anchoring element 4 and the shaft 2, while a relative rotational movement of these two parts about the longitudinal axis 2 as axis of rotation is still possible. The retaining ring 44 may be present in various embodiments. For example, the cross-sectional surface of the retaining ring 44, viewed orthogonally to the longitudinal axis 3, may be circular (FIG. 2c), rectangular (FIG. 2d), beveled (FIG. 2e to 2h) or also graded.

Figure 2I:
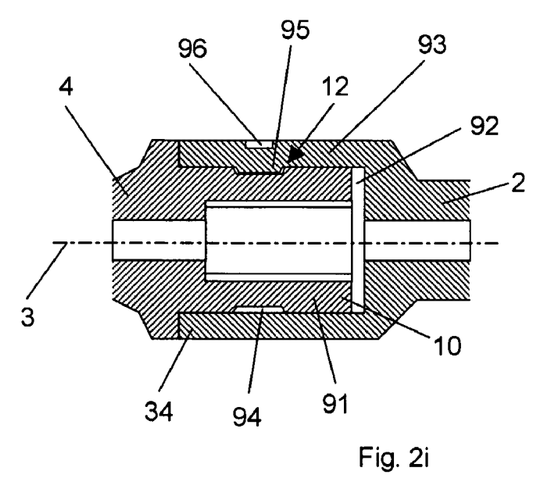
FIG. 2i shows a diagrammatic representation of the axial locking-in-position means of the embodiment of the inventive bone fixation means shown in FIG. 1d.
Figure 2K:
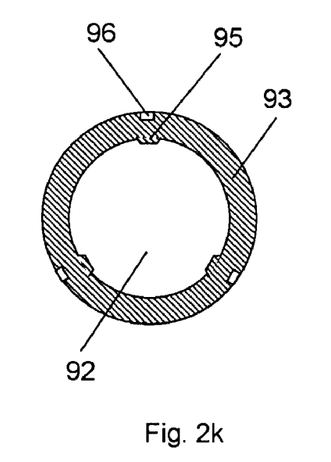
FIG. 2k shows a section, orthogonal to the longitudinal axis, through the sleeve of the axial locking-in-position means shown in FIG. 2i

In the embodiment, shown in FIGS. 2i and 2k, the locking-in-position means 12 are realized owing to the fact that the fixed end 10 of the anchoring element 4 comprises a circularly cylindrical connecting piece 91, which extends coaxially with the longitudinal axis 3 and is accommodated suitably in a circularly cylindrical opening 92, which is also coaxial with the longitudinal axis 3, of a sleeve 93, which is disposed at the fixed end 34 of the shaft 2. The connecting piece 91 is provided with a notch 94, which extends over the whole of the periphery. After the connecting piece 91 is introduced into the opening 92, several, preferably three depressions 95 are produced in the wall of the sleeve 93 by plastic deformation. The depressions 95 narrow the cross-sectional area of the opening 92 orthogonally to the longitudinal axis 3, and engage the notch 94. By making impressions 96 in the wall of the sleeve 93 before the assembly with the shaft 2, the shape of the depressions 95 can be controlled so that the connecting piece 91 is locked axially relative to the sleeve 93, while, at the same time, the connecting piece 91 in the sleeve 93 is mounted so that it can be rotated nevertheless about the longitudinal axis 3.

Aside from the axial locking-in-position means 12 (FIGS. 2a to 2k), the coupling 37 (FIG. 1) comprises the interacting means 5; 6, by means of which the relative rotation about the longitudinal axis 3 between the anchoring elements 4 and the shaft 2 can alternatively be locked or unlocked.

FIGS. 3a to 3g shows different embodiments of couplings 37, which make a frictional locking of the relative rotational movement between the shaft 2 and the anchoring element 4 possible.

Figure 1A:
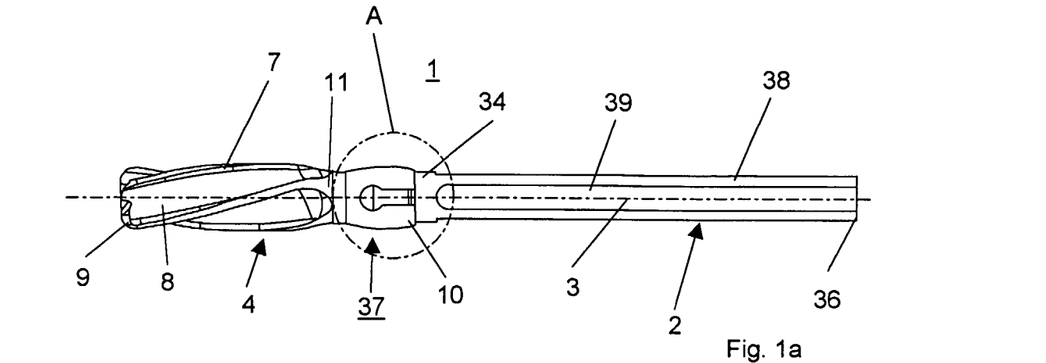
FIG. 1a shows a side view of an embodiment of the inventive bone fixation means.
Figure 1B:
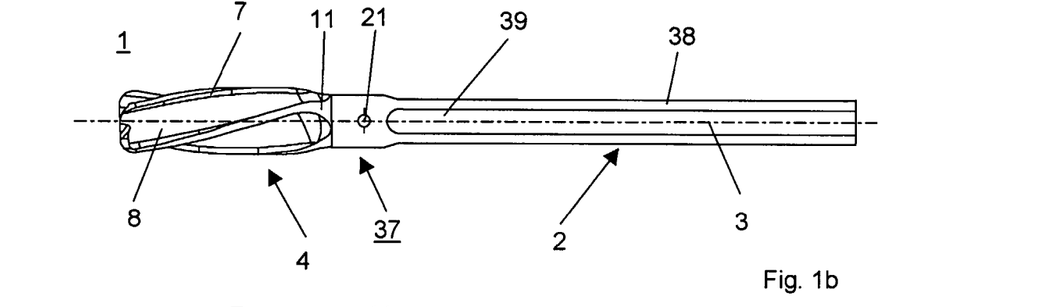
FIG. 1b shows a side view of a further embodiment of the inventive bone fixation means.
Figure 1C:
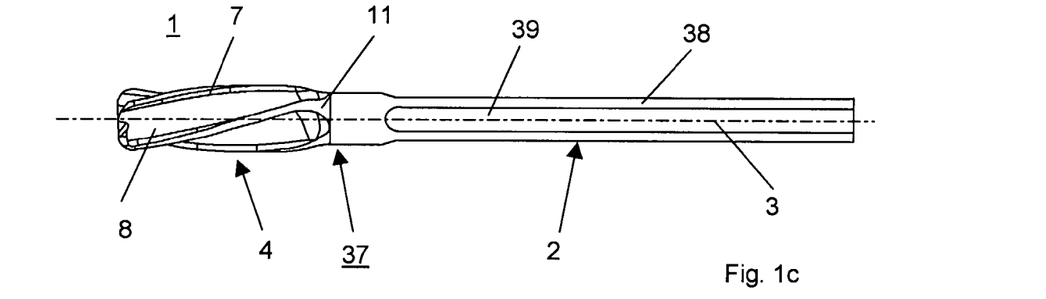
FIG. 1c shows a side view of yet another embodiment of the inventive bone fixation means.
Figure 1D:
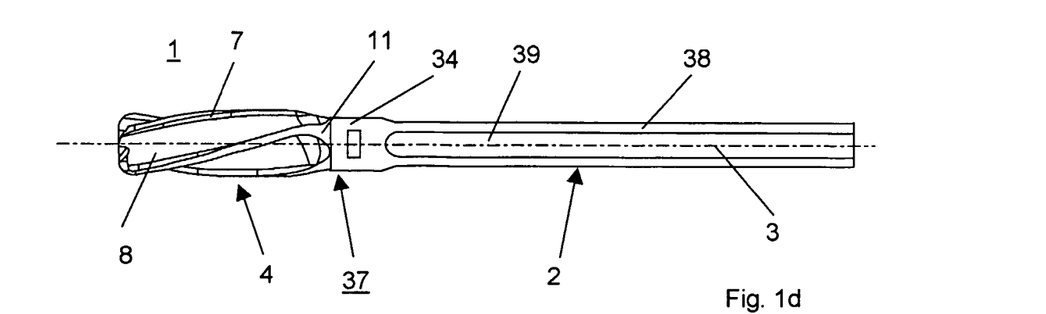
FIG. 1d shows a side view of a different embodiment of the inventive bone fixation means.
Figure 3A:
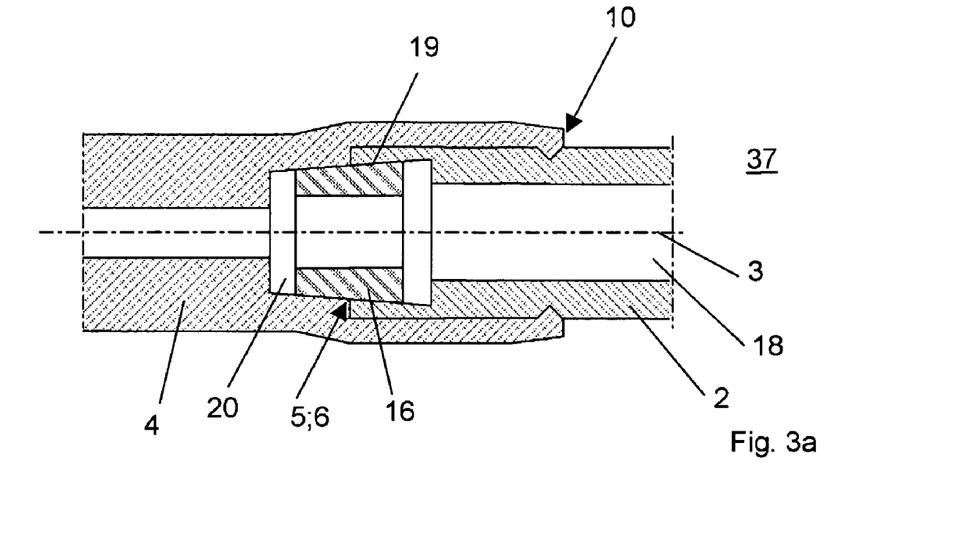
FIG. 3a shows an enlarged section of the circle A in FIG. 1a, FIG. 3b shows a section, similar to that of FIG. 3a, of a different embodiment of the inventive bone fixation means.

In FIG. 3a, the coupling 37 comprises, as first interacting means 5, a conical element 16, which is coaxial with the longitudinal axis 3, and, a second interacting means 6, a conical borehole 17, which is complementary to the conical element 16, in the shaft 2 and in the anchoring element 4. Moreover, the transition between the first inner conical segment 19 of the borehole 18, which is disposed in the shaft 2, and a second inner conical segment 20, which is disposed in the anchoring element 4, is continuous. The conical element 16 is mounted in the conical segments 19; 20, so that it can be shifted axially. The inner conical segments 19; 20, as well as the conical element 16 expand towards the fixed end 10 of the anchoring element 4. By means of a bolt (not shown), which can be passed through the central borehole 18 in the shaft 2, the conical element 16 can be pressed with the help of an additional instrument, such as a hammer, against the free end 9 (FIG. 1) of the anchoring element 4, until it is wedged in the two inner conical segments 19; 20. In order to make the wedging possible with the least expenditure of force, the conical element 16 is slotted in the longitudinal direction. Since the conical element 16 is wedged in both inner conical segments 19; 20, the shaft 2 and the anchoring element 4 are connected frictionally with one another in the wedged position of the conical element 16 and blocked to prevent any relative rotation. In this embodiment, however, the conical element 16 cannot be loosened once again.

Figure 3B:
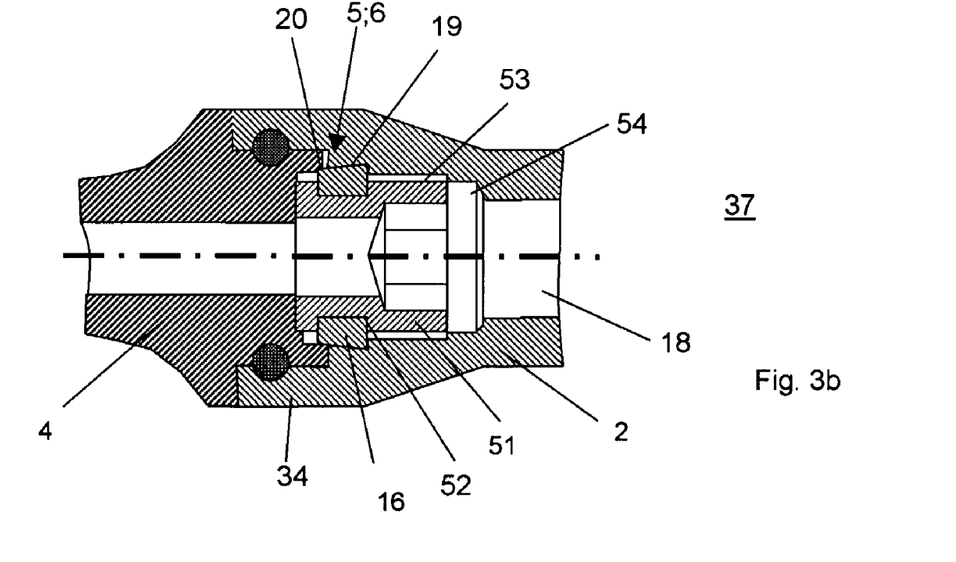

The embodiment of the interacting means 5; 6, shown in FIG. 3b, differs from the embodiment of the interacting means 5; 6 shown in FIG. 3a only in that the conical element 16 can be pressed against the free end 9 (FIG. 1) of the anchoring element 4 not with the help of an additional instrument (FIG. 3a), but with the help of a screw element 51, which has been introduced into the shaft 2. Over the whole of its length, the conical element 16 is captured axially in a peripherally extending groove 52 at the screw element 51, but can rotate freely relative to the screw element 51. The screw element 51 can be screwed into an internal thread 53 of a cylindrical expansion 54 of the borehole 18, which is disposed at the fixed end 34 of the shaft 2.

Figure 3C:
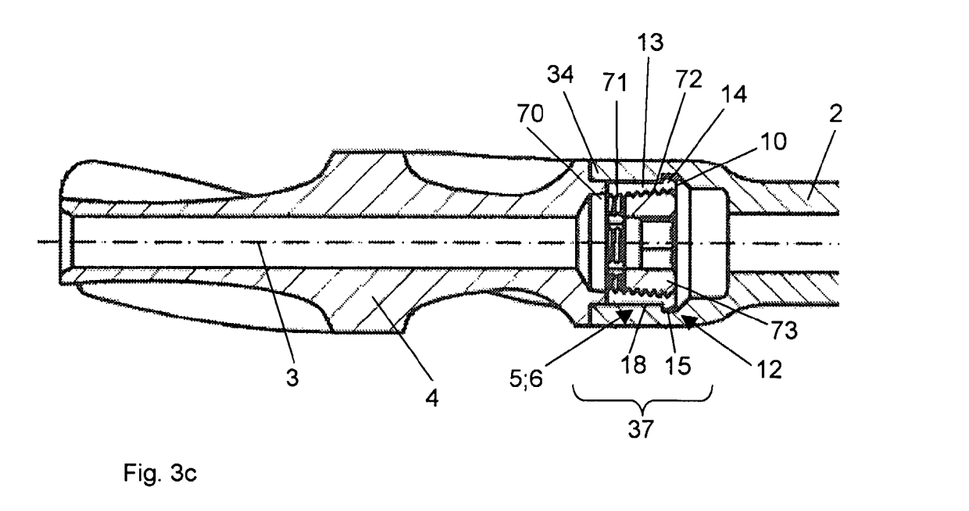
FIG. 3c shows a longitudinal section through the bone anchoring element and the fixed end of the shaft of a different embodiment of the inventive bone fixation means.

FIG. 3c shows an embodiment of the coupling 37, the interacting means 5; 6 of which can be locked by friction. The axial locking-in-position means 12, similar to the embodiment shown in FIG. 2a, is constructed as radially elastic blades 13. However, they differ owing to the fact that they are not pushed over the fixed end 34 of the shaft 2, but, instead, are disposed in the central borehole 18 in the shaft 2. The radial elevations 14 moreover are disposed on the outside at the blades 13 and at the groove 15 in the central borehole 18. The blades 13 enclose a cavity 70, which is coaxial with the longitudinal axis 3 and the wall of which has a conical inner thread 71, into which a locking screw 73, which has a complementary external thread 72, can be screwed. When the locking screw 73 is tightened, the blades 13, as first interacting means 5, are pressed radially against the wall of the borehole 18, which is suitable as the second interacting means 6. As a result, the shaft 2 is connected rotationally frictionally with the anchoring element 4. Since the elevations 14 at the blades 13 engage the groove 15, even when the blades 13 are not expanded, the actions of the axial locking-in-position means 12 and the interacting means 5; 6 are independent of one another. On the other hand, the axial locking-in-position means 12 and the interacting means 5; 6 are not constructed independently of one another here.

Figure 3D:
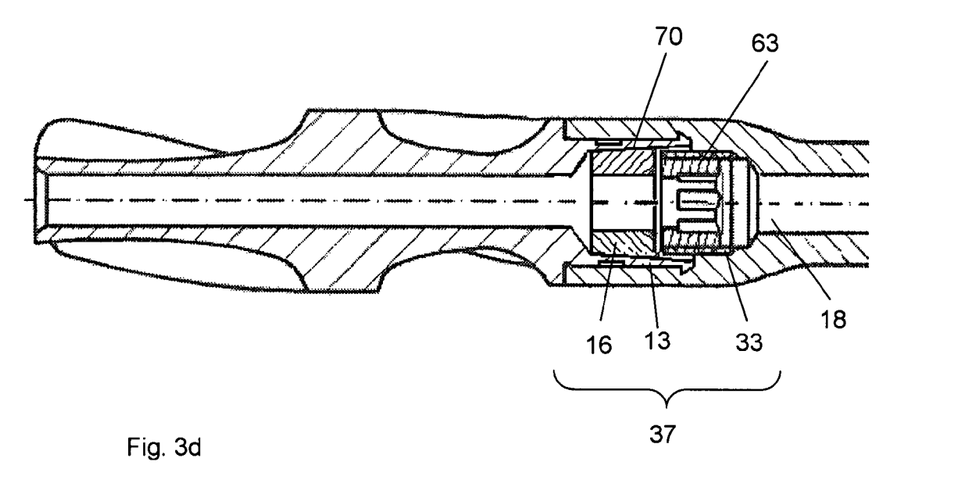
FIG. 3d shows a longitudinal section through the bone anchoring element and the fixed end of the shaft of a further embodiment of the inventive bone fixation means, FIG. 3e a perspective view of the bone anchoring element of, once again, a further embodiment of the inventive bone fixation means.

The embodiment of the coupling 37, shown in FIG. 3d, differs from the embodiment shown in FIG. 3c only therein that the conical cavity 70, surrounded by the blades 13, has a smooth wall, so that a conical element 16, complementarily conical, can be wedged in the cavity 70 by means of a locking screw 63. The conical element 16 is pressed axially by a locking screw 63, which can be screwed into an internal thread 33 disposed in the borehole 18, into the cavity 70.

Figure 3E:
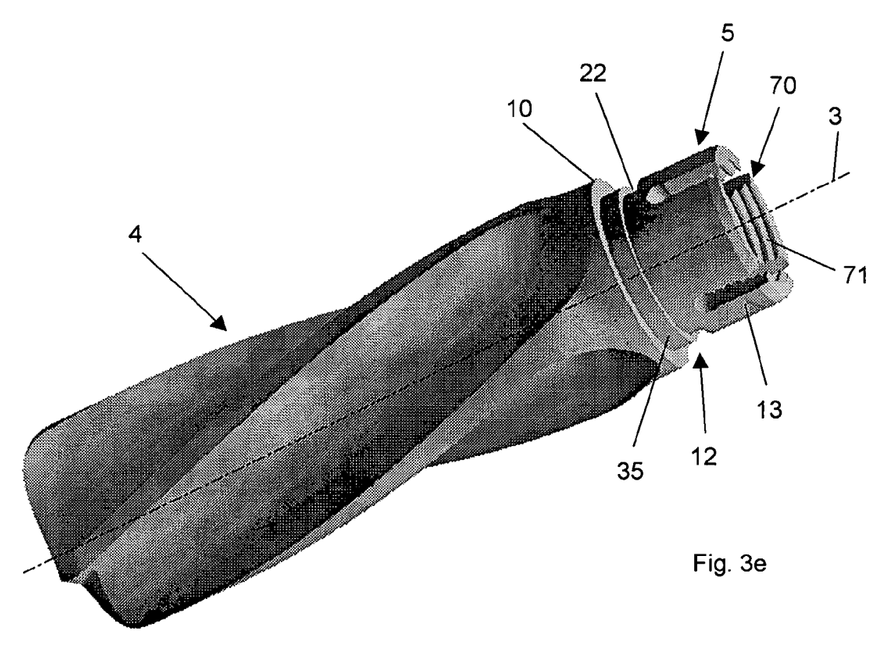

In the case of the embodiment, shown in FIG. 3e, the axial locking-in-position means 12 and the interacting means 5; 6, are developed independently of one another. The axial locking-in-position means 12 are constructed similarly to the embodiment shown in FIG. 2b, that is, a peg 35 with a recess 22, which is concentric with the longitudinal axis 3, for the radial accommodation of locking-in-position pins 21 (FIG. 2b) is disposed at the fixed end 10 of the anchoring element 4. The configuration of the interacting means 5; 6 differs from the embodiment shown in FIG. 3c only in that the first interacting means 5 are disposed terminally at the peg 35 and surround the radially elastic tabs 13 without elevations 14.

Figures 3F, 3G:
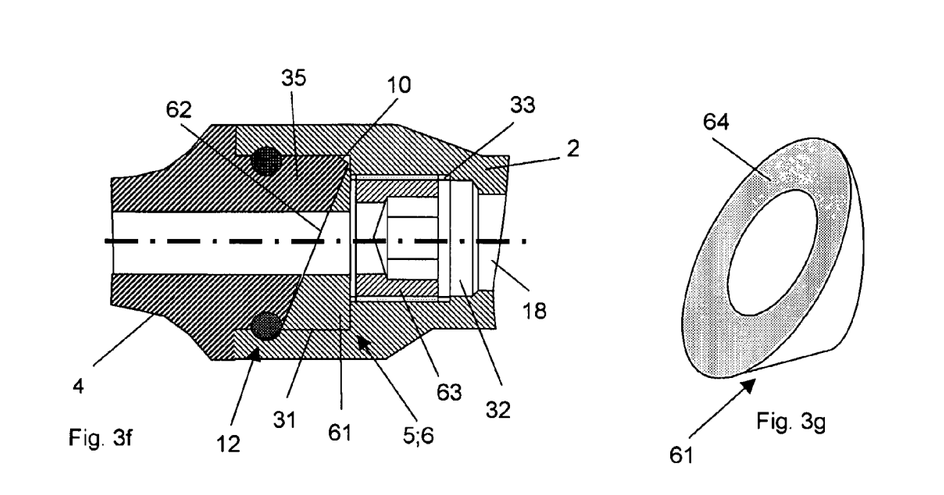
FIG. 3f shows a section, similar to that of FIG. 3a, of once again a different embodiment of the inventive bone fixation means.
FIG. 3g shows a perspective representation of the wedge element of the embodiment of the inventive bone fixation means, shown in FIG. 3d.

The embodiment, shown in FIGS. 3f and 3g, differs with respect to the interacting means 5; 6 from the embodiment shown in FIG. 3b therein that, as first interacting means 5, instead of the conical element 16 (FIG. 3a), an asymmetric, wedge-shaped clamping elements 61 is disposed in the first expansion 31 of the central borehole 18 of the shaft 2. This wedged-shaped clamping elements 61, having a tapered front surface 64, is pressed against a complementary taper 62 at the peg 35 of the clamping element 44 for blocking purposes. As a second interacting means 6, a locking screws 63, by means of which the wedged-shaped clamping element 61 can be pressed against the taper 62 at the fixed end of the anchoring element 4, is disposed in the second expansion 32 of the central borehole 18 in the shaft 2, the second expansion 32 having an internal thread 33 here. The axial locking-in-position means 12 is realized similarly to the embodiment shown in FIG. 2c.

Figure 4A:
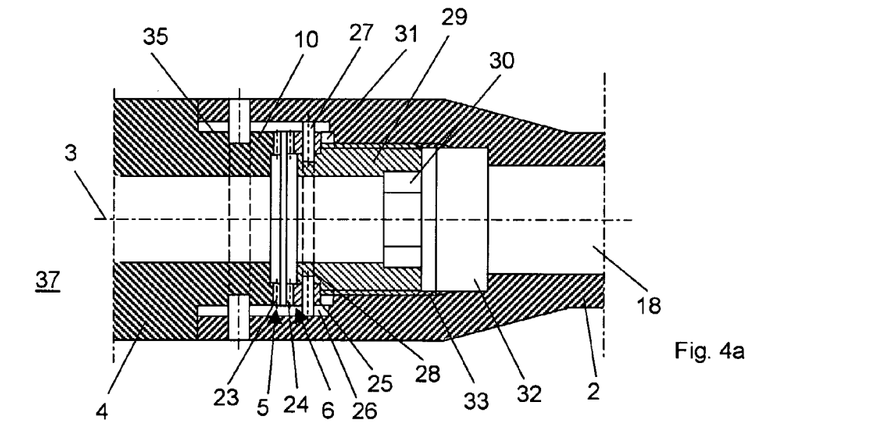
FIG. 4a shows a section, similar to that of FIG. 3a, of a further embodiment of the inventive bone fixation means.
Figure 4B:
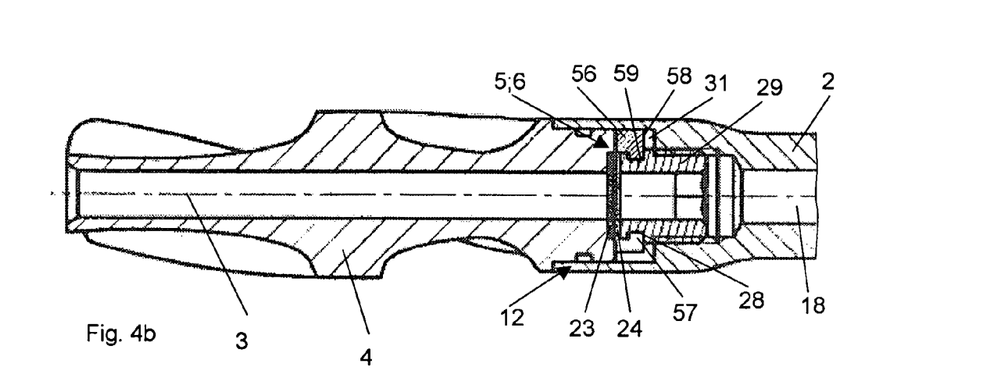
FIG. 4b shows a longitudinal section through the bone anchoring element and the fixed end of the shaft of a further embodiment of the inventive bone fixation means.
Figure 4C:
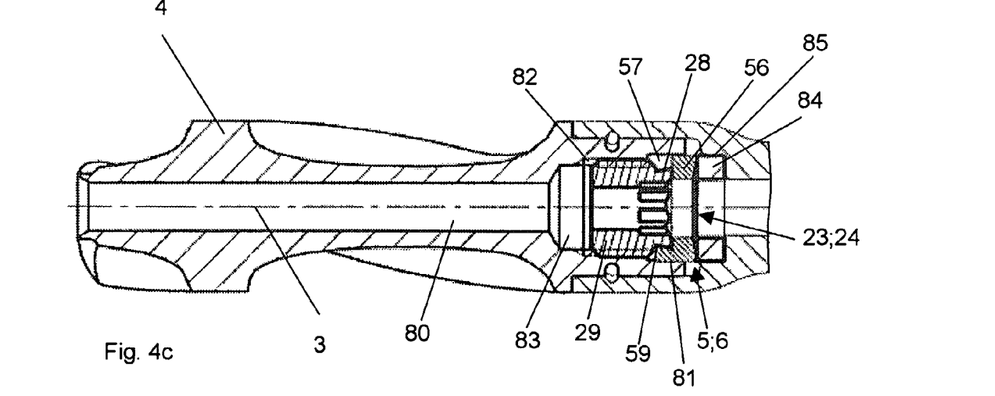
FIG. 4c shows a longitudinal section through the bone anchoring element and the fixed end of the shaft of a different embodiment of the inventive bone fixation means.
Figure 4D:
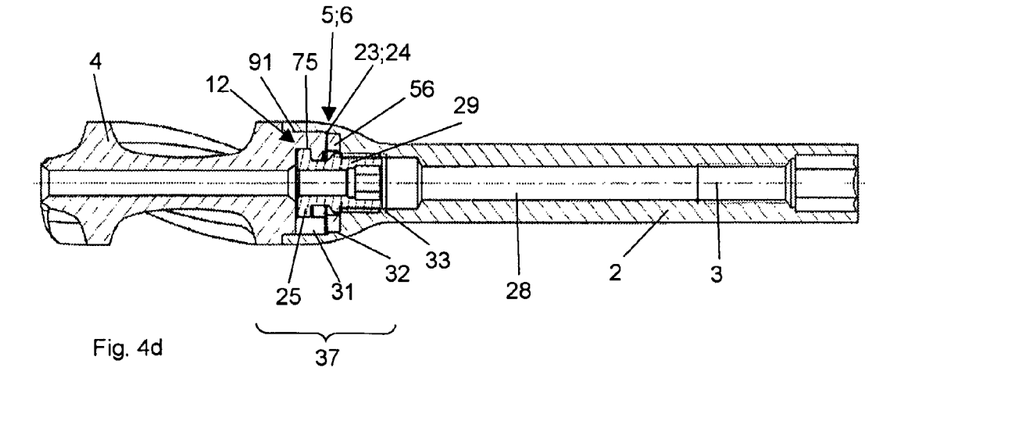
FIG. 4d shows a longitudinal section through a further embodiment of the inventive bone fixation means and FIG. 5 shows a partial section through the inventive fixation device, implanted in the femur.

Different embodiments of couplings 37, which comprise interacting means 5; 6 for a positive locking of the relative rotational movement of the shaft 2 and the anchoring element 4, are shown in FIGS. 4a and 4d.

For the embodiment of the interacting means 5; 6, shown in FIG. 4a, the anchoring element 4 has at its fixed end 10 a peg 35, which tapers in diameter and can be introduced axially into an expanded segment 35 in the central borehole 18 of the shaft 2 and, at its front surface orthogonal to the longitudinal axis 3, has a first denticulation 23. The peg 35, which is provided with the first denticulation 23, forms the first of the interacting means 5 here, whereas the second of the interacting means 6 is formed by the axially displaceable fixation element 56, which is mounted in the first expanded segment 31. The fixation means 56, which is constructed ring-shaped here, has a second denticulation 24 at the face surface facing the anchoring element 4. The two denticulations 23; 24 can be caused to engage or disengage by axially shifting this fixation element 56. The shifting of the fixation element 56 is accomplished axially in both directions by a screw 29, which can be shifted in the internal thread 33, mounted in the second expanded segment 32, by rotating the screw in the clockwise or counterclockwise direction. The means 30 serve to accommodate a screwdriver and may be constructed, for example, as a hexagon drive or a TORX drive. The dimensions are such that a screwdriver (not shown) can be passed from the free end 36 (FIG. 1) of the shaft 2 through the central borehole 18 in the shaft 2 and brought into engagement with the means 30.

The fixation element 56 is axially displaceable in the direction of the longitudinal axis 3, whereas rotation about the longitudinal axis 3 is prevented. For the embodiment shown in FIG. 4a, the fixation element 56 comprises two pins 27, which are disposed diametrically opposite to one another and pass through the wall of the fixation element 56 and the tips of which are captured axially in a second annular groove 28 at the screw 29, so that the screw 29 can be rotated about the longitudinal axis 3, while rotation of the fixation element 56 about the longitudinal axis 3 is prevented by the rear ends of the pins 27, which are guided in the two longitudinal grooves 26, which extend parallel to the longitudinal axis 3 in the inner wall of the first expanded segment 31.

The embodiment of the interacting means 5; 6, shown in FIG. 4b, differs from the embodiment of the interacting means 5; 6, shown in FIG. 4a only in that an out-of-round fixation element 56, which preferably is oval when viewed in a cross section orthogonal to the longitudinal axis 3 and which is rotationally fixed in a complementarily equipped, first expanded segment 31 of the central borehole 18 in the shaft 2, is provided. The fixation element 56 has an indentation 57, orthogonal to the longitudinal axis 3, so that the U-shaped fixation element 56, before the installation of the screw 29, can be shifted in the borehole 18 in the shaft 2 transversely to the longitudinal axis 3 over the screw 29. At its rear end 58, the indentation 57 has a constriction 59, which can be pushed transversely to the longitudinal axis 3 into the second annular groove 28. The fixation element 56 is connected axially firmly with the screw 29 by means of this constriction 59, which is inserted into the second annular groove 28, whereas the screw 29 can be rotated relatively to the fixation element 56 about the longitudinal axis 3.

FIG. 4c shows an embodiment of the interacting means 5; 6, which differs from the embodiment, shown in FIG. 4b only in that the fixation element 56 is taken up in a terminally disposed, first expanded segment 81 of the central borehole 80 in the anchoring element 4. Viewed in the cross-section orthogonal to the longitudinal axis 3, the fixation element 56 as well as the first expanded segment 81 have an oval cross-sectional surface, so that the fixation element 56 is prevented from rotating about the longitudinal axis 3, but is taken up axially displaceable in the first expanded segment 81. Similarly to FIG. 4b, the fixation element 56 has an indentation 57, which is orthogonal to the longitudinal axis 3, so that the fixation element 56, which is constructed U-shaped, can be shifted transversely to the longitudinal axis 3 over the screw 29. The indentation 57 also has a constriction 59 here, which can be shifted transversely to the longitudinal axis 3 into the annular groove 28, so that the fixation element 56 is connected axially fast with the screw 29, the rotation of the screw 29 not being hindered. The screw 29 can be screwed here into an internal threat 82, which is disposed in a second, expanded segment 83 of the central borehole 80 in the anchoring element 4. Furthermore, an oval annular element 84 is disposed in a complementary, oval recess 85 in the central borehole 18 in the shaft 2 and also secured against rotation about the longitudinal axis 3 by the oval configuration of the ring element 84 and the recess 85. The two denticulations 23; 24, which can be brought into engagement with one another, are mounted at the two adjacent front surfaces at the fixation element 56 and at the ring element 84, so that the denticulations 23; 24 can be engaged or disengaged by the axial displacement of the fixation element 56 by means of the screw 29.

The embodiment of the interacting means 5; 6, shown in FIG. 4d, differs from the embodiment of the interacting means 5; 6, shown in FIG. 4, only in that an out-of-round fixation element 56, which preferably is oval when viewed in a cross section orthogonal to the longitudinal axis 3, is provided, which is rotationally fixed in a complementarily configured, first expanded segment 31 of the central borehole 18 in a shaft 2. At the fixed in 10 of the anchoring element 4, a circularly cylindrical connecting piece 91, which is coaxial with the longitudinal axis 3, is disposed and can be introduced into a complementarily constructed second expansion 32 of the central borehole, which is disposed at the fixed end 34 of the shaft 2. At the front face, this connecting piece 91 has a first denticulation 23, which can be brought into engagement with a second denticulation 24, which is disposed at the opposite front face of the fixation element 56. For this purpose, the coupling 37 comprises a screw 29, which can be screwed into an internal threat 33 in the central borehole 18. At its end facing the anchoring element 4, the screw 29 has a screw head 25 of larger diameter, which can be pushed transversely to the longitudinal axis 3 into a guide 75, which is radially open at one side, and can be fastened there so that it is axially fixed but free to move rotationally. When the screw 29 is tightened, on the one hand, the shaft 2 is pressed axially against the anchoring element 4, as the result of which the function of the axially locking-in-position means 12 is assumed by the screw 29, and, on the other, the two denticulations 23; 24 are brought into engagement, so that, in the embodiment shown here, the axial locking-in-position means 12 and the interacting means 5; 6 are not independent of one another.

Accordingly, for the embodiments of the interacting means 5; 6, shown in FIGS. 4a to 4d, when the denticulations 23; 24 engage one another, the shaft 2 and the anchoring element 4 are rotationally coupled positively and, when the denticulations 23; 24 are disengaged, the shaft 2 can be rotated relative to the anchoring element 4 about the longitudinal axis 3.

Figure 5:
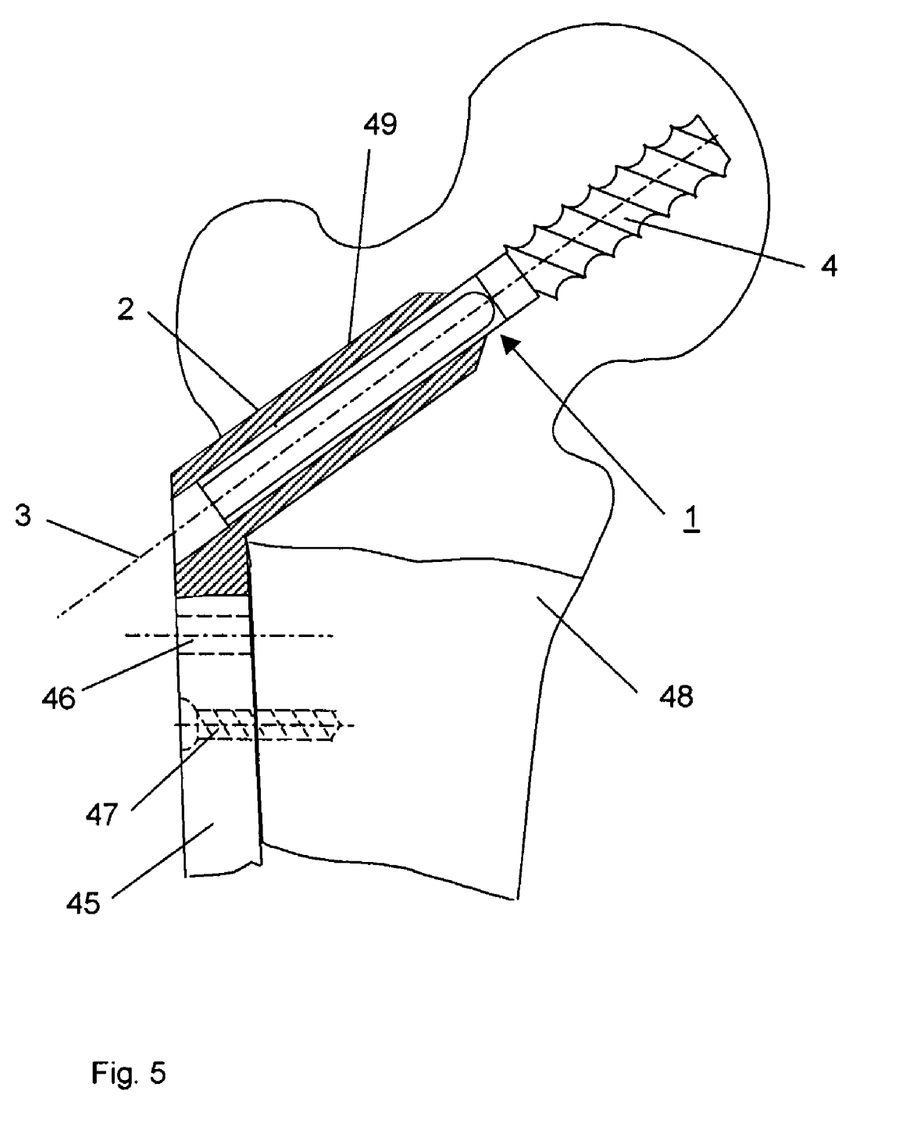

As shown in FIG. 5, the sleeve tab 45 can be fastened by means of bone screws 47, which are to be introduced into the boreholes 46 laterally to the femur 48, whereas the guide sleeve 49 comes to lie laterally at the neck of the femur fracture or the trochanteric fracture. Accordingly, with the help of the bone fixation means 1, the head fragment can be fixed rotationally stably with the rest of the femur 48.

The surgical technique for implanting the bone fixation means consists therein that by means of an instrument and in one step, several boreholes of different diameter for bringing the bone fixation means 1 and the guide sleeve 49, mounted at the sleeve tab 45, into the center of the neck of the femur, can be produced in the lateromedial direction below the large trochanter;

subsequently, the bone fixation means 1 is rotated or hammered into the neck of the femur, the correct depths for hammering or screwing it in being determined by a targeting device, after which the guide sleeve 49 of the sleeve tab 45 is pushed over the shaft of the bone fixation means and aligned at the femur shaft;

the sleeve tab 45 is fixed to the bone shaft with the help of bone fixation means 20 constructed as bone screws and the rotational movement of the shaft 2 and the anchoring element 4 is blocked by means of an instrument.

The invention claimed is:

1. A bone fixation implant comprising:
   a longitudinal shaft having a first end, a second end, and a central longitudinal axis;
   an anchoring element at the first end of the shaft, the anchoring element configured and dimensioned for engaging bone; and
   a rotational coupling element provided at an interface between the anchoring element and the shaft, the coupling element configured and dimensioned to permit free rotation of the anchoring element relative to the shaft about the central longitudinal axis when in a first position and rotationally lock the anchoring element to the shaft when in a second position.

2. The implant of claim 1, further comprising an axial connection element disposed at an interface between the anchoring element and the shaft, the axial connection element preventing a relative securing of the anchoring element to the shaft along the central longitudinal axis.

3. The implant of claim 2, wherein the axial connection element and the rotational coupling element are separate structures.

4. The bone fixation implant of claim 1, wherein the anchoring element is detachably connected to the shaft.

5. The bone fixation implant of claim 2, wherein the axial connection element includes a plurality of spaced-apart, elastic tabs.

6. The bone fixation implant of claim 5, wherein the elastic tabs include projections that engage a complementary, circular groove concentric with the longitudinal axis.

7. The bone fixation implant of claim 6, wherein the elastic tabs are disposed on the anchoring element and the groove is disposed at the shaft.

8. The bone fixation implant of claim 6, wherein the projections have a convex shape.

9. The bone fixation implant of claim 6, wherein the groove has a V-shaped cross section.

10. The bone fixation implant of claim 2, wherein the axial connection element includes a pin fixed transversely to the longitudinal axis, and the pin engages a complementary circular groove concentric with the longitudinal axis.

11. The bone fixation implant of claim 2, wherein the axial connection element includes a retaining ring that engages a first annular groove at the shaft and a second annular groove at the anchoring element, the first and second annular grooves concentric with the longitudinal axis.

12. The bone fixation implant of claim 1, wherein the rotational coupling element rotationally locks the shaft and the anchoring element through a frictional connection.

13. The bone fixation implant of claim 1, wherein the rotational coupling element includes
   a hollow, conical volume disposed coaxially with the longitudinal axis at an interface between the shaft and the anchoring element, and
   a conical wedge configured and dimensioned for axial movement within the conical volume,
   wherein movement of the conical wedge in a first direction within the conical volume frictionally locks the shaft relative to the anchoring element.

14. The bone fixation element of claim 13, wherein the hollow, conical volume includes a first conical volume provided in the shaft and a second corresponding conical volume provided in the anchoring element.

15. The bone fixation implant of claim 1, wherein the rotational coupling means includes:

a plurality of radially elastic blades disposed at the anchoring element configured and dimensioned for insertion within a central borehole at the first end of the shaft; and a conical locking screw configured and dimensioned to press the elastic blades against an inner wall of the central borehole to rotationally lock the shaft to the anchoring element.

16. The bone fixation element of claim 15, wherein the radially elastic blades include projections configured and dimensioned to engage a complementary circular groove at the shaft concentric with the longitudinal axis.

17. The bone fixation implant of claim 1, wherein the rotational coupling element rotationally locks the shaft and the anchoring element through a positive connection.

18. The bone fixation implant of claim 17, wherein the rotational coupling element includes a first denticulation at the anchoring element configured and dimensioned to engage a second denticulation at the shaft.

19. The bone fixation implant of claim 18, wherein the second denticulation is axially-displaceable for engagement with the first denticulation.

20. The bone fixation implant of claim 19, wherein the second denticulation is axially displaced by means of a screw.

21. The bone fixation implant of claim 1, wherein the anchoring element includes a plurality of helical blades having a pitch.

22. The bone fixation implant of claim 21, wherein the pitch is greater than 50 mm.

23. The bone fixation implant of claim 1, wherein the shaft has a non-circular cross-section.

24. A bone fixation system comprising:

a bone plate configured and dimensioned for attachment to a femur, the bone plate including an angular sleeve with a non-circular cross-section adapted to receive a bone fixation implant;

a bone fixation implant configured and dimensioned for use with the bone plate, the bone fixation implant including a shaft having a first end, a second end, and a central longitudinal axis;

an anchoring element at the first end of the shaft, the anchoring element having a plurality of helically-twisted blades for engaging bone;

an axial connection element disposed at an interface between the anchoring element and the shaft, the axial connection element preventing axial movement of the anchoring element relative to the shaft along the central longitudinal axis; and a rotational coupling element disposed at an interface between the anchoring element and the shaft, the coupling element configured and dimensioned to permit free rotation of the anchoring element with respect to the shaft about the central longitudinal axis when in a first position and rotationally lock the anchoring element to the shaft when in a second position.

25. A method for repairing a bone fracture comprising:

inserting a bone fixation implant into a fractured bone, the bone fixation implant including:

a shaft having a first end, a second end, and a central longitudinal axis;

an anchoring element at the first end of the shaft, the anchoring element configured and dimensioned for engaging the bone;

a rotational coupling element configured to permit free rotation of the anchoring element with respect to the shaft about the central longitudinal axis when in a first position and rotationally lock the anchoring element to the shaft when in a second position;

inserting a bone plate having a sleeve keyed to mate with the shaft of the bone fixation implant over the shaft of the bone fixation implant;

aligning the bone plate with the fractured bone; and moving the rotational coupling element into the second position to rotationally lock the anchoring element to the shaft.

* * * * *